(12) United States Patent
Utsugi

(10) Patent No.: US 7,896,816 B2
(45) Date of Patent: Mar. 1, 2011

(54) SKIN TEST DEVICE

(75) Inventor: Ryuichi Utsugi, Tokyo (JP)

(73) Assignee: DRDC Limited, Tokyo (JP)

( * ) Notice: Subject to any disclaimer, the term of this patent is extended or adjusted under 35 U.S.C. 154(b) by 2608 days.

(21) Appl. No.: 10/228,058

(22) Filed: Aug. 27, 2002

(65) Prior Publication Data

US 2004/0044294 A1 Mar. 4, 2004

(51) Int. Cl.
*A61B 5/00* (2006.01)
(52) U.S. Cl. .................................................... 600/556
(58) Field of Classification Search ................ 600/583, 600/181, 556, 573; 604/46, 43, 47; 606/167
See application file for complete search history.

(56) References Cited

U.S. PATENT DOCUMENTS 4,802,493 A * 2/1989 Maganias ................... 600/556
5,179,959 A * 1/1993 Fishman et al. ............. 600/556
2002/0169394 A1* 11/2002 Eppstein et al. ............. 600/573

* cited by examiner

*Primary Examiner*—Max Hindenburg
*Assistant Examiner*—Fangemonique Smith
(74) *Attorney, Agent, or Firm*—Edell, Shapiro & Finnan, LLC

(57) ABSTRACT

Skin test device has a film backing. The film backing is made of silicone, and is marked off into divisions by grooves. The divisions each have a different sample containing a suspected allergen. The film backing has a see-through feature and the condition of the skin can visually be checked when the film backing is staying on the skin. The divisions are easily separable from each other. When certain samples cause significant allergic reactions, the divisions corresponding to those samples can be removed immediately.

20 Claims, 6 Drawing Sheets

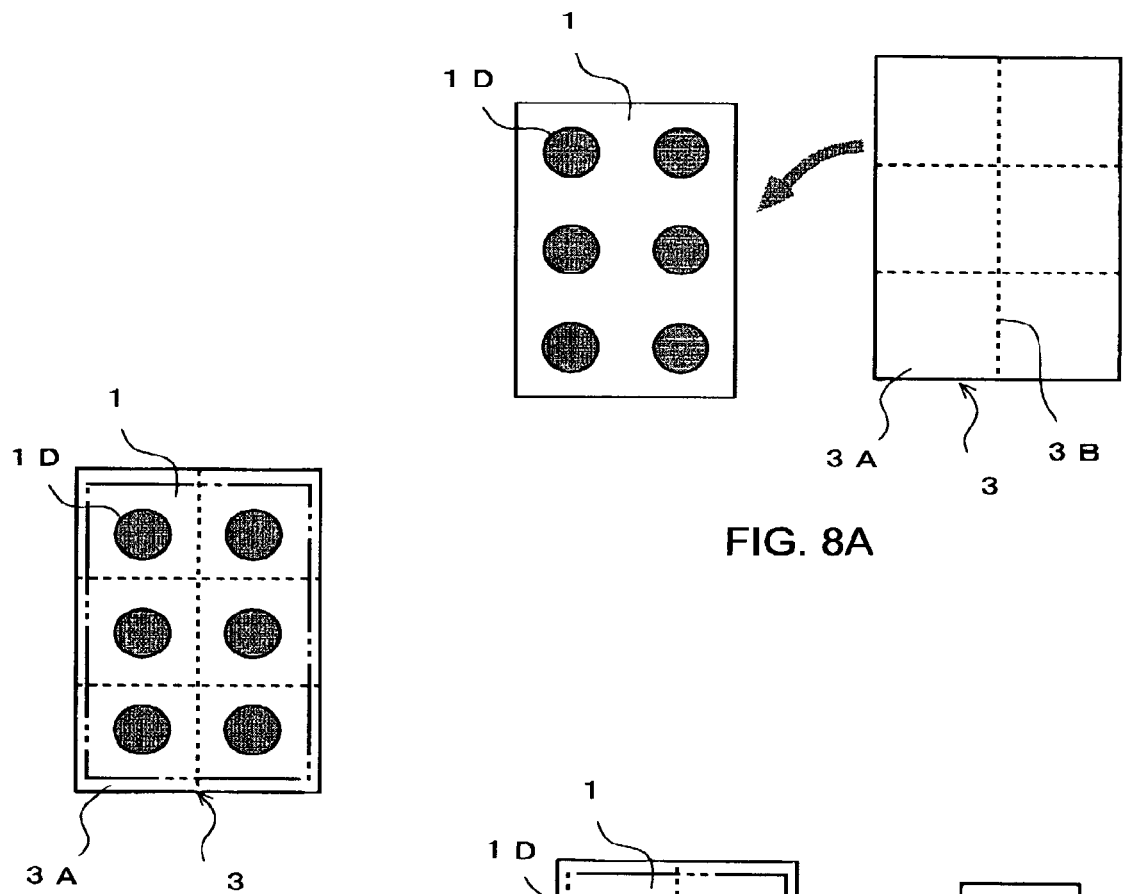
FIG. 8A
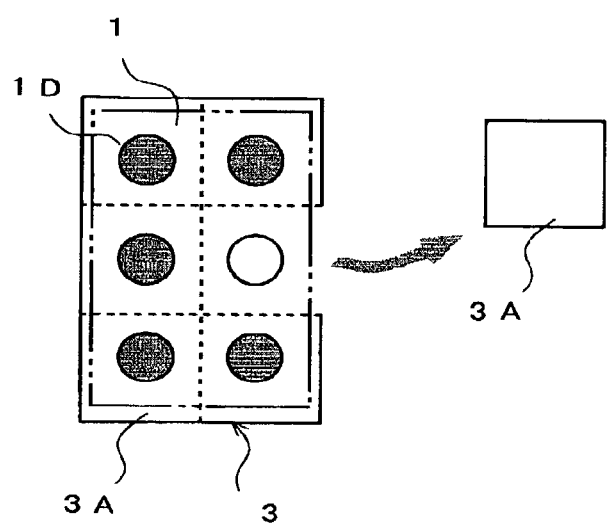
FIG. 8B
FIG. 8C

SKIN TEST DEVICE

BACKGROUND OF THE INVENTION

The present invention relates to a skin test device that is used for patch testing and other variables to determine an allergen (antigen) which is associated with contact dermatitis, asthma or food allergy and which triggers eczema, dermatitis or drug eruption.

In the modern world where many different chemicals are commonly and widely used, diseases caused by uptake of or contact with chemicals become more and more common. For example, it is well known that allergic symptoms such as eczema may occur as a result of skin contact with chemicals in cosmetic preparations or accessories such as necklaces or pierces. Such a skin reaction is called "contact dermatitis".

A prevention against the contact dermatitis as well as asthma and food allergies is to identify the causative substance, i.e., allergen, and avoid exposure to it. Patch testing is widely used for this purpose. In patch testing, a suspected allergen is prepared in a solvent such as water or vaseline. The sample is placed on the skin and kept for a given period of time. Hives or blisters indicates a positive response. The substance contained in the sample is identified as the subject's allergen.

Patch testing may require application of a sample in an adequate concentration to the skin. Direct application of the sample to the skin of a subject has, however, many problems in conjunction with formulation and operations of application. With this respect, more convenient and easier approaches have been used to place samples on the skin. Ready-to-use skin test devices are typical examples in which suspected allergen is provided already applied to a fabric or a plastic panel. Some ready-to-use skin test devices comprise two or more samples of suspected allergens that are consistently placed thereon in order to test for the allergens together.

As apparent from the above, skin test devices significantly decrease troubles associated with patch testing. However, these skin test devices are not perfect.

A major problem of the conventional skin test devices is impossibility to observe the skin condition during their staying on the skin. A patch test may be continued even under the condition that a causative allergen can be identified from hives or blisters. This problem is more noticeable for a ready-to-use device that contains several samples because skin normally responds to different suspected allergens in various degrees. When a patch test is continued until allergic reactions develop fully for all allergens, undesirable reactions such as blisters can occur as a result of excessive exposure to allergens highly prone to cause the allergic reactions. Higher levels than is necessary for the identification tend to cause blisters on the skin, which may cause after-effects such as pigmentation. This is not desirable on the aesthetic and health considerations of the subject.

In a sense, such situations stem from a longer response time (e.g., 48 hours) that is required for certain allergens to cause hives or blisters on the skin of a subject. Taking this issue into consideration, some approaches place samples in the skin via small scratches or pricks in order to develop reactions to the allergens for a shorter period of time. The time required for reaction is reduced by means of delivering the samples into the body. Pricking the skin before application of the samples is rather troublesome. It is cumbersome to consistently prick the skin at the exact locations where samples should be placed especially when these samples are ready-to-use on a single skin test device.

A broad object of the present invention is to solve the problems associated with conventional skin test devices and make this kind of skin testing widely popularized.

More specifically, it is an object of the present invention to provide a skin test device that does not cause excessive skin reactions during testing.

It is another object of the present invention to provide a skin test device with which skin testing can be done for a shorter period of time without reducing the precision of the test.

SUMMARY OF THE INVENTION

A skin test device according to the present invention that solves the above-mentioned problems is embodied by the following two aspects of the invention.

A first aspect of the invention is described. The first aspect of the invention can be classified broadly into the following two sorts. In the description below, these sorts of the first aspect are referred to as the "aspect 1-1" and the "aspect 1-2" for convenience.

The aspect 1-1 is a patch test device comprising a film backing and a sample that is placed on one surface of the film backing, the sample containing a suspected allergen, wherein the film backing is see-through or transparent from either side or from only one side to the other of the film backing at least at the portion where the sample is placed.

This patch test device allows visual confirmation of the surface of the skin through the film backing when the device stays on the skin for patch testing, at least at the portion where the skin is in contact with the sample. Accordingly, patch testing can be terminated immediately after allergic reactions are developed enough to cause hives or blisters and to ensure identification of causative allergens for allergen samples that are responsible for the reactions. This eliminates the risk of excessive exposure of the subject's skin to the suspected substances, contributing to better safety of patch testing.

Another patch test device that contains no sample also has similar features and advantages to those obtained in the above-mentioned patch test device, though it requires a bit more effort for sample application. More specifically, such a patch test device comprises a film backing; an adhesive layer provided at a predetermined position on one surface of the film backing to secure the film backing to the skin of a subject; and at least one keeper region that is provided on one surface of the film backing, the keeper region is for keeping a sample that contains a suspected allergen, wherein the film backing is see-through from either side or from only one side to the other at least at the portion corresponding to the keeper region. In this case, the film backing may be transparent.

The keeper region may be a depression or a concave portion formed in one surface of the film backing. Alternatively, the keeper region may be keeper that is provided on one surface of the film backing to keep the sample. The keeper may be provided inside the depression. Examples of the keeper include cotton, hydrogels, and agar-like materials.

As described above, the film backing according to the aspect 1-1 is see-through or transparent from either side or from only one side to the other at least at the portion where the sample is placed.

The see-through features in the context of the present invention indicate that the condition of the skin can be observed through the film backing while the patch test device is staying on the skin.

The portion of the film backing where the sample is placed may be completely transparent. Alternatively, it may be translucent, semi-transparent, or even clear-colored to the extent that the condition of the skin can be visually checked. The portion may be either single-layered or multi-layered as long as the above-mentioned requirement is satisfied. For example, the film backing may comprise a layer to keep the shape of it and a layer to keep samples. In addition, the film backing may comprise a layer of a sheer mesh of a non-transparent or opaque material as long as the condition of the skin can be visually checked without removing the patch test device.

As apparent from the above, the see-through feature of the film backing is required to be provided at least the portion where the sample is placed. Alternatively, the entire surface of the film backing may have such a see-through feature. The whole see-through film backing may simplify the configuration, reducing associated costs and fees.

The see-through feature may be achieved by using silicone. Silicone is a clear material that has the capacity to be formed into various shapes with different surface properties depending on a processing method used. Accordingly, silicone materials are well suitable for the film backing of the present invention. For example, a silicone material is formed into a film with one surface having adhesiveness and the other surface having rigidity like a cured resin. A sample containing a suspected allergen is placed on the sticky surface. This provides a single-layered film backing, simplifying the configuration of the patch test device. Of course, the overall film backing may be made of silicone. Examples of other suitable materials for the film backing include resins such as urethane, acrylic, vinyl or nylon resins.

As described above, a depression or a concave portion may be formed in one surface of the film backing. Alternatively, keeper may be provided on one surface to keep samples to be tested for. With a depression formed in the surface, the sample is to be placed in that depression. This makes it possible to prevent the sample from spreading excessively when the patch test device is staying on the skin. The keeper also serves to prevent the sample from spreading excessively.

The film backing may contain only a single sample. Alternatively, the film backing may contain two or more samples placed at different areas on the backing. The aspect 1-1 marks off the film backing into a plurality of divisions each of which includes a different sample on one surface thereof. This makes the different samples to be tested for together and is therefore preferable. The divisions are not necessarily to be visually recognizable.

For patch test devices containing no sample, the above-mentioned keeper regions are provided in individual divisions.

In the patch test device that contains different samples placed on different divisions in the film backing, the divisions may be configured so that they can easily be separated from each other. Since the film backing has the divisions that are arranged continuously but easily separable from each other, the division over the site where allergic reactions are observed can be removed easily when necessary. Patch testing can be terminated immediately after allergic reactions are developed enough to cause hives or blisters and to ensure identification of causative allergens for allergen samples that are responsible for the reactions. Other samples to be tested for may be left on the skin. It should be noted that appropriate testing can be performed for each of different samples. The samples are not required to be spread over the entire surface of the divisions.

The divisions may be provided in any patterns on the film backing. For example, the film backing may be marked off into a matrix of divisions. This fully uses the area of the film backing without any losses. The adjacent divisions are separated from each other by, for example, perforations. Alternatively, these divisions may be separated by grooves that do not penetrate through the film backing.

Next, the aspect 1-2 is described.

The aspect 1-2 is a patch test device comprising a film backing; and an adhesive layer provided at a predetermined position on one surface of the film backing to secure the film backing to the skin of a subject, at least one hollow space being provided in the film backing at a predetermined position, the hollow space having such a size that is required to place a sample containing suspected allergen on the skin while keeping the film backing stay on the skin, wherein the film backing is see-through at least along the periphery of the hollow space.

This patch test device is secured to the skin and a sample is placed on the exposed skin through the hollow space formed on the film backing. In other words, the hollow space serves to hold and keep the sample on the skin, reducing the labor for patch testing. The film backing of the skin test device is see-through at least along the periphery of the hollow space. The condition of the skin can be visually checked without removing the patch test device from the skin. As in the aspect 1-1, this patch test device also eliminates the risk of excessive exposure of the subject's skin to the suspected substances, contributing to better safety of patch testing.

The number of the hollow spaces is not specifically limited. It is determined based on the number of the samples to be tested for.

The size of the hollow space is so that the sample can be placed appropriately on the skin. For example, a cylindrical hollow space may be provided that is 5 mm to 20 mm in diameter.

The patch test device according to the aspect 1-2 may comprise a see-through cover film that is adapted to be placed over the other surface of the film backing so that the hollow space is covered with the cover film while the film backing is secured to the skin, the cover film being for preventing the sample placed on the skin from running out of the hollow space.

The cover film contributes to avoiding adhesion of samples to clothes of a person or other portions of the skin that are not intended to be subjected to patch testing. The cover film has a see-through feature in order not to deteriorate the above-mentioned effect of eliminating excessive exposure of the subject's skin to samples that are to be tested for. The cover film should be as clear as the condition of the skin can be observed. It may be fully transparent, translucent, semi-transparent, or even clear-colored.

When the film backing has two or more hollow spaces formed therein, the cover film may extend over all hollow spaces. In such a case, the cover film may be marked off into two or more cover sections that correspond to the respective hollow spaces. The cover sections are easily separable from each other. Accordingly, the section corresponding to the sample that causes significant allergic reactions can be removed easily when necessary. Patch testing can be terminated immediately after allergic reactions are developed enough to ensure identification of causative allergens for allergen samples that are responsible for the reactions. After the identification, the allergen samples in the hollow space can be removed appropriately, while leaving other samples on the skin to continue the test.

Keeper may be provided inside the hollow space to keep the sample. The keeper may be, for example, cotton, hydrogel, or an agar-like material.

The keeper may be any one of keepers as long as the sample can be kept appropriately. For example, the keeper may be a see-through type keeper. This eliminates the risk of the keeper of blocking the observation of the skin.

While the aspect 1-2 has been described in conjunction with a case where the cover film is not integral with the film backing, they may be combined as a unit. The patch test device for such a case comprises, for example, a cover film which covers the entire surface of the film backing and which is integrally fixed to the other surface of the film backing. A sample is placed on the portion of the cover film facing to the hollow space in the film backing. By combining the cover film with the film backing as a unit and previously placing a sample on the portion of the cover film facing to the hollow space of the film backing, a convenient ready-to-use patch test device is provided as in the patch test device in the aspect 1-1.

Of course, the keeper may be provided inside the hollow space.

When the cover film is combined with the film backing as a unit and the film backing has two or more hollow spaces formed therein, the cover film is provided so that it covers these hollow spaces. The cover film is marked off into two or more cover sections that correspond to the respective hollow spaces. The cover sections are easily separable from each other so that the separated cover section can be removed from the film backing. The cover section that is placed on the site where significant allergic reactions are caused can be removed when necessary. Therefore, patch testing can be terminated immediately after allergic reactions are developed enough to ensure identification of causative allergens for allergen samples that are responsible for the reactions. After the identification, the allergen samples in the hollow space can be removed appropriately, while leaving other samples to be tested for on the skin.

Regardless of whether the cover is combined with the film backing as a unit, the film backing of the patch test device according to the aspect 1-2 may have the following configuration. A projected rim is formed from other portion on one surface of the film backing along the open edge of the hollow spaces in one surface of the film backing. The adhesive layer is provided on the end surface of the projected rim. The projected rims eliminate or reduce the problem of sample leakage. When the contact surface between the film backing having the adhesive layer and the skin is relatively large, the film backing tends to be affected by the irregularities in the skin surface. Gaps may often be formed between the film backing and the skin surface. The sample may run out of the hollow space through the gaps and extend over the skin surface. By providing the above-mentioned projected rim and the adhesive layer is provided on the end surface thereof, the contact surface between the film backing and the skin can be reduced in size. The reduction in size of the contact surface contributes to solving the problem of the sample leakage.

The second aspect is as follows.

The second aspect is a prick test device comprising a film backing; a sample that is placed on one surface of the film backing, the sample containing a suspected allergen; and pricking bit formed on one surface of the film backing in the area where the sample is placed, the pricking bit helping to make a prick in the skin of a subject when the film backing is secured to the skin.

Since the prick test device comprises the pricking bit on the surface on which the sample is placed, an appropriate prick or scratch can be formed in the skin only by means of sticking the prick test device or applying an adequate pressure to the device after it is stuck on the skin. In this event, the pressure may be applied by rubbing the surface of the film backing. This prick test device eliminates the necessity of a separate process of pricking the skin before the device is put on the skin, reducing the time for the skin testing. The above-mentioned pricking bit is provided at the corresponding position where the sample is placed. The sample always comes over the prick in the skin. No alignment between the prick and the sample is required, which reduces the labor for skin testing.

The pricking bit may be any one of suitable means as long as it can facilitate to prick the skin. For example, the pricking bit may be a pin-shaped member, a needle-shaped member, a blade-shaped member or a combination thereof. For a pin-shaped pricking bit, two or more pins may be bundled together. The pin may be, for example, protruded by 0.05 mm to 1.5 mm from the surface of the film backing where the sample is placed.

The pricking bit may be transparent. This reduces the possibility of the pricking bit to block or hinder visual checking of the skin condition.

The pricking bit of the present invention may be removable while the prick test device is staying on the skin. A subject may feel discomfort if the pricking bit is kept in contact with the skin for a long time. The discomfort can be reduced by means of making the pricking bit removable and removing it immediately after pricking.

The pricking bit may be removed through any configuration. For example, the pricking bit may be a pin-shaped member having the tip which is protruded from one surface of the film backing and the base which is connected to remover disposed on the other surface of the film backing so that the remover is removable from the film backing, wherein the pin-shaped member can be removed by means of removing the remover from the film backing.

The pricking bit may comprise two or more pin-shaped members with each pin-shaped member being connected to a single remover. All pricking bit may be removable at once only by means of removing the single remover from the film backing.

The second aspect of the present invention may be implemented alone. Alternatively, it may be combined with the above-mentioned aspect 1-1. For example, at least the portion on the film backing where the sample is placed may be see-through from either side or from only one side to the other. The entire surface of the film backing may have such a see-through feature.

The second aspect may be combined with a skin test device in which different samples are placed in different areas on the film backing. In such a case, the pricking bit may be provided for each of the areas where the samples are placed.

BRIEF DESCRIPTION OF THE DRAWINGS

FIG. 8 is a view illustrating how the skin test device in FIG. 3 is used.

DETAILED DESCRIPTION OF THE PREFERRED EMBODIMENTS

Figure 1:
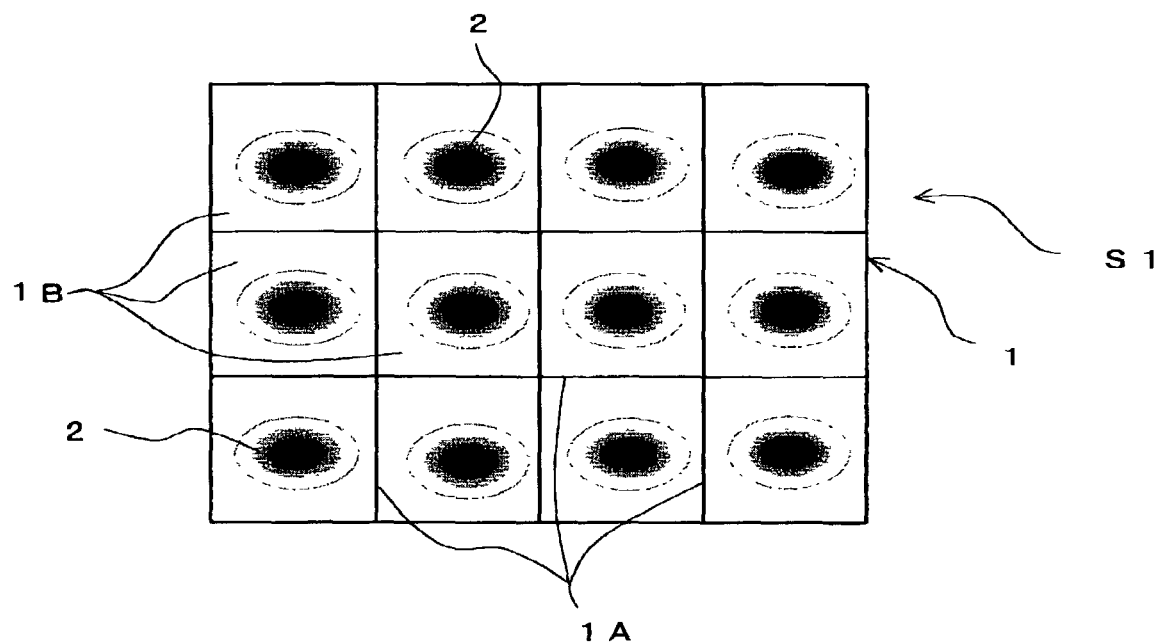
FIG. 1 is a plan view showing a surface of a skin test device according to a first embodiment of the present invention.

Now, first, second, and third embodiments of a skin test device according to the present invention are described with reference to the drawings.

In the following description, the same components and parts are depicted by the identical reference numerals and redundant multiple descriptions thereof are omitted.

The skin test device according to the first embodiment is described with reference to FIGS. 1 to 4, the skin test device according to the second embodiment is described with reference to FIGS. 5 and 6, and the skin test device according to the third embodiment is described with reference to FIGS. 7 and 8.

First Embodiment

Figure 2:
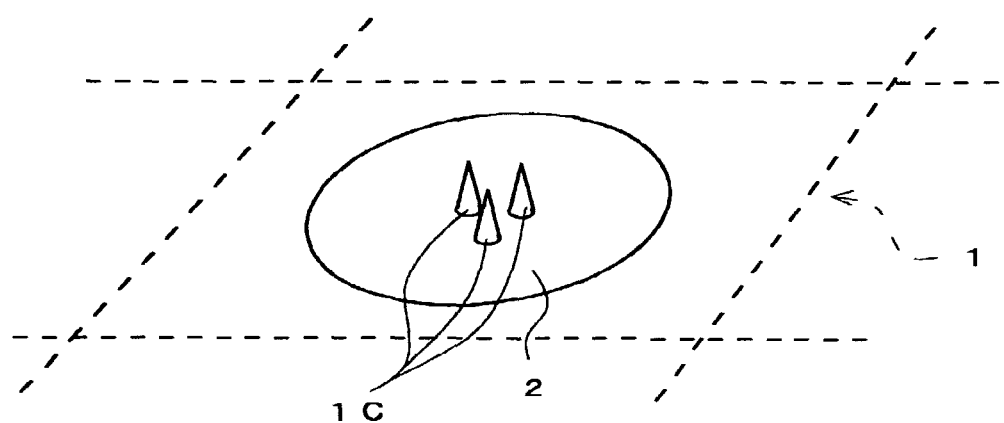
FIG. 2 is an enlarged perspective view showing the back surface of the skin test device in FIG. 1.
Figure 3:
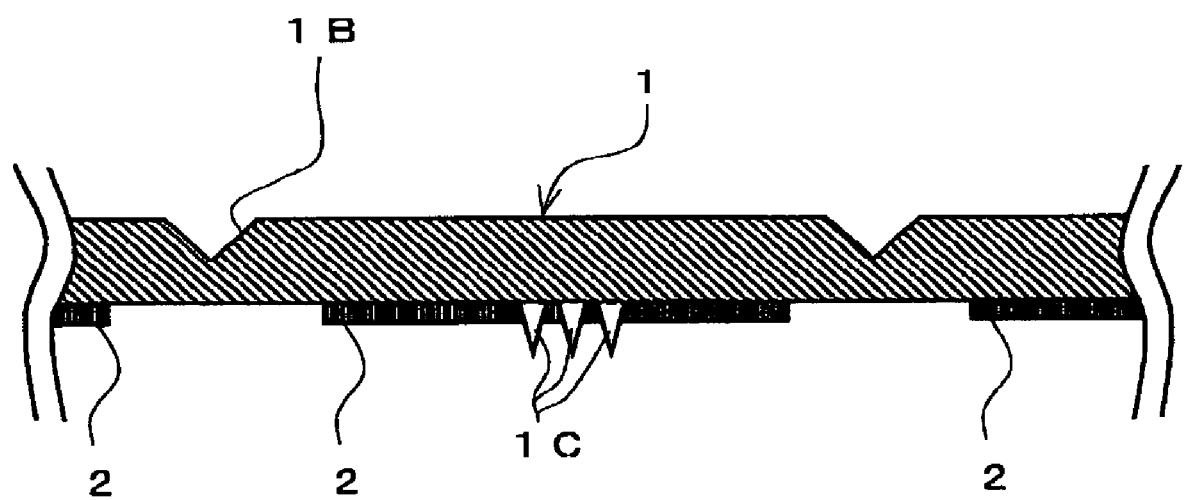
FIG. 3 is a cross-sectional view of the skin test device in FIG. 1, which is taken along the thickness of the skin test device.

The skin test device according to the first embodiment is as shown in FIGS. 1 to 3. FIG. 1 is a plan view showing a surface of a skin test device S1. FIG. 2 is an enlarged perspective view showing the back surface of the skin test device S1. FIG. 3 is a cross-sectional view of the skin test device S1.

The skin test device S1 in this embodiment comprises a film backing 1 that is made of silicone to have a certain see-through feature over the entire surface thereof, and a plurality of samples 2 that are placed on one surface of the film backing 1.

The samples 2 may or may not be on the film backing at the time of manufacture or delivery of the skin test device S1. For the skin test device S1 on which no samples 2 are placed at the time of manufacture or delivery, the samples 2 are placed before use to provide a skin test device as described below.

The film backing 1 in this embodiment has a rectangular shape. However, the shape of the film backing may arbitrarily be selected depending on, for example, the site where the skin test device S1 is to be stuck.

The back surface of the film backing 1 (on which the samples 2 are placed) is processed to have a predetermined adhesiveness. This allows the film backing 1 to keep the sample 2 on the back surface thereof. The top surface of the film backing 1 (opposite to the surface where the samples 2 are placed) is less sticky. It is similar to a surface of the plastic film for easier handling of the skin test device S1.

Grooves 1A are formed in the surface of the film backing 1 in vertical and horizontal directions. Each groove 1A has the depth smaller than the thickness of the film backing 1 so that the grooves 1A do not penetrate through the film backing 1. The grooves 1A define rectangular divisions 1B on the film backing 1. Each side of the divisions 1B may be, but not limited to, about 1 to 2 cm in length in this embodiment.

In this embodiment, the film backing 1 is marked off into a matrix of the divisions 1B by the grooves 1A that are formed along the boundaries of the divisions 1B.

The film backing 1 made of silicone can be easily separated with fingers. The grooves 1A ensure removal of a given division 1B when necessary without undesirably breaking off the film backing 1. In this context, some or all grooves 1A may be replaced with perforations to define the divisions 1B.

The samples 2 contain different suspected allergens from each other. The suspected allergens may be selected from those that are to be tested for. For example, chemicals contained in cosmetic preparations may be selected as suspected allergens to identify a causative agent to the contact dermatitis due to cosmetic ingredients. In other words, all or some suspected ingredients that are allowed to be used in cosmetic preparations, such as preservatives or surfactants, may be used as suspected allergens to identify a causative agent of the contact dermatitis due to cosmetic ingredients. These suspected allergens are prepared in water or in vaseline to prepare liquid or gel samples 2.

The samples 2 are placed over a predetermined range in the divisions 1B. The samples may be placed on either the entire surface or a part of the divisions 1B. The regions on which the samples 2 are placed each function as the keeper region in the present invention. Of course, some regions may be left without any samples.

Pin-shaped members 1C, which serve as pricking bit in the present invention, are formed in the region on which the samples 2 are placed in each division 1B on the back surface of the film backing 1 in this embodiment. The pin-shaped member 1C is an aid to prick the skin when the film backing 1 is stuck to the skin. The pin-shaped members 1C may be made of, for example, iron, plastic, stainless steel, or titanium alloy. In this embodiment, the pin-shaped members 1C are made of a clear resin material. The length of the pin-shaped members 1C is determined depending on various factors such as the sites on the skin for which the skin testing is to be conducted. In this embodiment, pin-shaped members 1C are protruded from the surface of the film backing 1 by approximately 0.2 mm to 0.5 mm. The tip of the pin-shaped member 1C is as sharp as small scratches can be made in the surface of the skin when the film backing 1 is in contact with the skin. The number of the pin-shaped members 1C is not specifically limited. A single pin-shaped member 1C may be used. In this embodiment, a set of three pin-shaped members 1C are provided in the divisions 1B at the positions corresponding to the regions where the samples 2 are placed.

Figure 4:
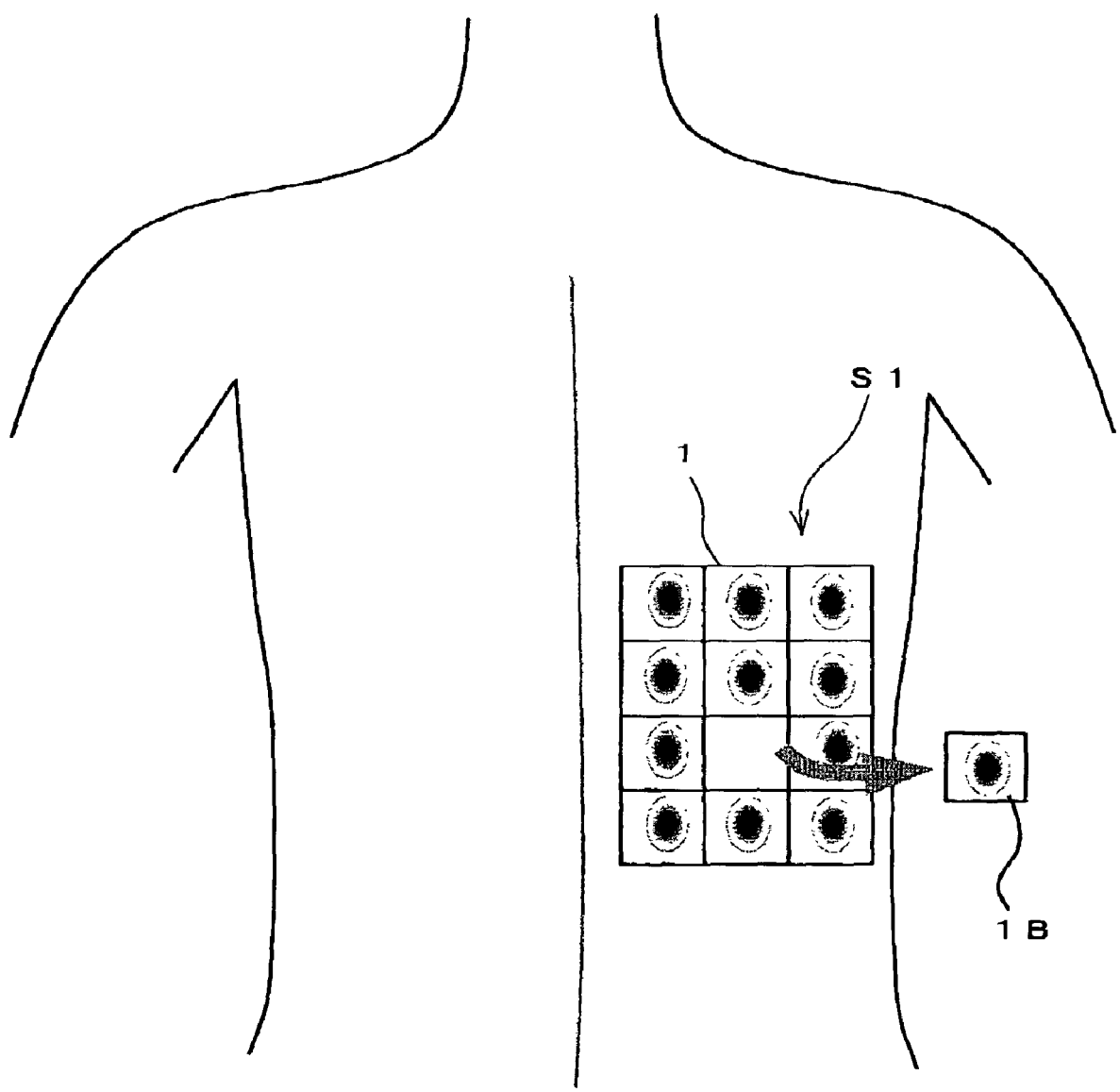
FIG. 4 is a view illustrating how the skin test device in FIG. 1 is used.

Now, an example of how to use the skin test device S1 is described. The skin test device S1 is designed to be stuck to a predetermined portion of the skin of a subject for which skin testing is to be conducted. For example, the skin test device S1 is usually stuck to the back or to the inside of forearm of a subject. The film backing 1 is sticky on the back surface thereof, so that the skin test device can be stuck to the skin without using any other adhesive materials or tapes. FIG. 4 shows the skin test device S1 staying on the back of a subject.

When the skin test device S1 is put on the skin and a slight pressure is applied to the film backing 1 if necessary, the pin-shaped members 1C that are protruded from the back surface of the film backing 1 make pricks or scratches in the skin at the positions corresponding to the divisions 1B. The samples 2 on the back surface of the film backing 1 then come to contact with the skin, covering over the pricks in the skin. This condition is similar to the one after the samples 2 are applied to the skin. After the lapse of a certain period of time, allergic reactions are developed which cause hives or blisters and which ensure identification of causative allergens for allergen samples 2 that are responsible for the reactions. Since the film backing 1 is made see-through, the change in skin condition can be visually observed throughout the test without removing the skin test device S1 staying on the skin.

When enough allergic reactions are developed to ensure identification of causative allergens for allergen samples 2 that are responsible for the reaction, the divisions 1B in which the allergen samples 2 are placed are removed. This eliminates the risk of excessive reactions to be caused on the skin of a subject. The divisions 1B with allergen samples 2 are removed one by one after the development of enough allergic reaction.

Patch testing is continued for regions where allergic reactions are not fully developed.

As a modification of the skin test device S1, a predetermined protective release liner may be disposed over the surface of the film backing 1 on which the samples 2 are placed. The protective release liner prevents evaporation of the samples 2. In addition, the liner covering the sticky surface facilitates handling of the skin test device S1.

The film backing 1 may be made of a clear resin material. For example, the film backing 1 may be made of an acrylic resin which is so flexible that the film backing 1 contours the irregularities in the skin. When the film backing 1 is made of a resin material, it is preferable that a keeper member be disposed on the portion of the film backing 1 where the samples 2 are placed. The keeper member serves as the keeper in the present invention and may be, for example, cotton, hydrogel, or an agar-like material. If clear or see-through keeper member is required, an agar culture medium may be used.

The film backing 1 may have a depression of the size that can receive the samples 2, in the region where the sample 2 is placed. The keeper member such as an agar culture medium may be received in the region in the film backing 1 where the sample 2 is to be placed, and the keeper may be soaked or impregnated with the sample 2 to be kept.

Second Embodiment

A skin test device according to this embodiment is generally identical to the skin test device that has been described in conjunction with the first embodiment. The way of use is also similar to the one that has been described in conjunction with the skin test device in the first embodiment.

A difference between the skin test devices of the fist and second embodiments is that pin-shaped members 1C in the skin test device according to the second embodiment can be removed from the film backing 1.

Figure 5:
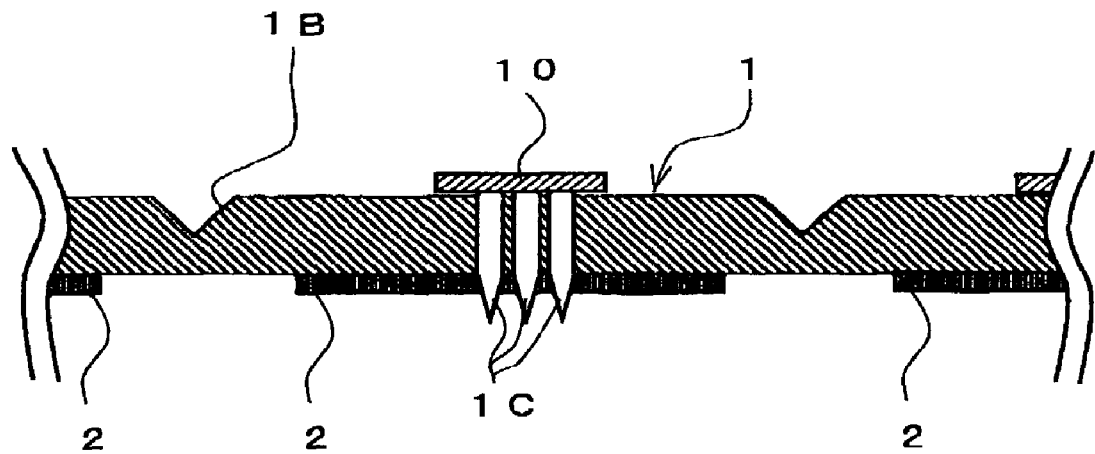
FIG. 5 is a cross-sectional view of a skin test device according to a second embodiment of the present invention, which is taken along the thickness of the skin test device.

The skin test device according to this embodiment comprises, as shown in FIG. 5, remover films 10 on the surface thereof. The remover film 10 corresponds to the remover in the present invention. Each remover film 10 is provided in the division 1B on the film backing 1 so that it is easily separable from the film backing 1. The remover films 10 are provided in the respective divisions on the film backing 1.

The pin-shaped members 1C of the skin test device according to this embodiment penetrate through the film backing 1. The tip of the pin-shaped member 1C is protruded from the film backing 1 by about 0.2 mm to 0.5 mm. The base of the pin-shaped member 1C is fixed to the remover film 10 on the associated division 1B.

Before use, the skin test device of this embodiment is stuck to the skin and a slight pressure may be applied to the film backing 1 to prick the skin. Then, the remover film 10 is removed. The pin-shaped members 1C that are fixed to the remover film 10 are all removed from the film backing 1 accordingly.

Figure 6:
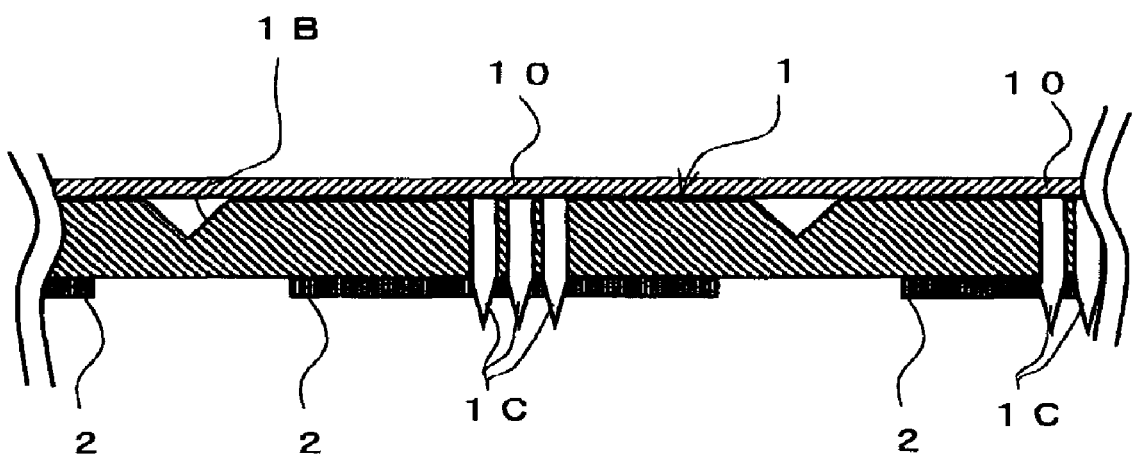
FIG. 6 is a cross-sectional view of a modified version of the skin test device according to the second embodiment of the present invention, which is taken along the thickness of the skin test device.

The remover films 10 may be combined with each other as a single cover film, as shown in FIG. 6. This allows removal of all pin-shaped members 1C through a single operation of removing one remover film 10.

Third Embodiment

A skin test device S2 according to a third embodiment is described.

Figure 7:
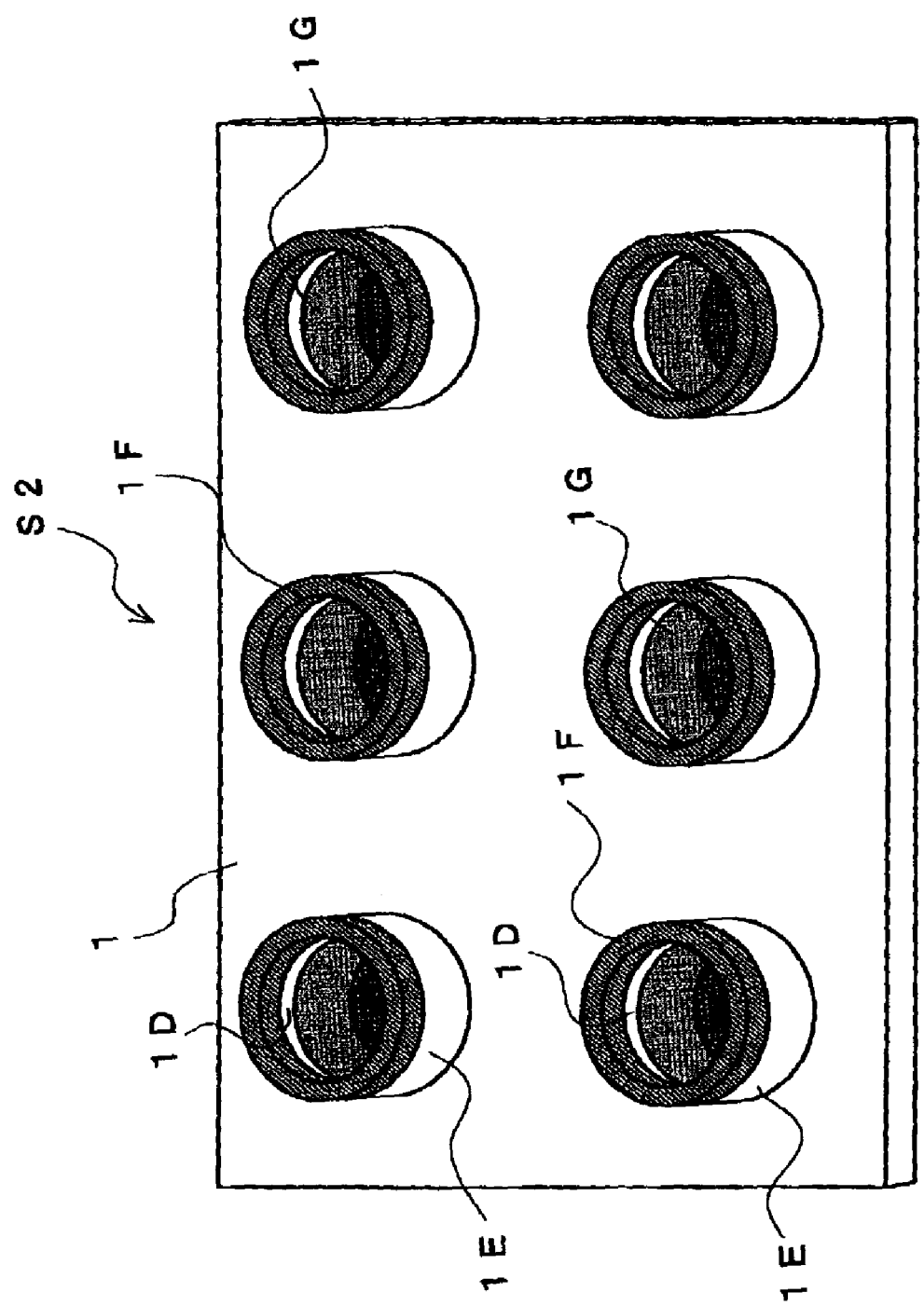
FIG. 7 is a perspective view of a skin test device according to a third embodiment of the present invention.

The skin test device S2 of this embodiment is as shown in a perspective view in FIG. 7. FIG. 7 is a perspective view of the skin test device S2, with the surface to be contacted with the skin facing upward.

The skin test device S2 of this embodiment comprises a film backing 1. The film backing 1 is made of a flexible resin material, such as an acrylic resin. Therefore, it can conform the irregularities in the skin. The entire surface of the film backing is clear to a certain extent. It is noted that the film backing 1 is required to be so clear that the surface of the skin can be visually checked through the film backing 1 when the film backing is staying on the skin.

The film backing 1 includes a matrix of hollow spaces 1D. In this embodiment, six hollow spaces 1D arc arranged into a matrix of two by three. The hollow spaces 1D are penetrated through the film backing 1. Each hollow space 1D has an enough size to allow for application of the sample 2 inside the hollow space with the skin test device S2 staying on the skin. The hollow space 1D in this embodiment is circular in cross-section having a diameter of about 1 cm. However, there is no limitation for the shape of the hollow space.

In the skin test device S2 in this embodiment, projected rims 1E are provided along the respective peripheries of the hollow spaces 1D on one surface of the film backing 1. The projected rim 1E is like a short cylinder to surround the outer periphery of the hollow space 1D. An adhesive layer 1F is provided on the open end surface of the projected rim 1E to stick the skin test device S2 to the skin.

Keeper members 1G are placed for keeping samples inside the respective hollow spaces 1D in the skin test device S2 of this embodiment. The keeper member 1G corresponds to the keeper in the present invention. The keeper member 1G may be, for example, cotton, hydrogel, or an agar-like material as described above. In this embodiment, hydrogel is used for the keeper members 1G.

The skin test device S2 of this embodiment also comprises a rectangular cover film 3 that is formed as a separate unit from the film backing 1, as shown in FIG. 8. The cover film 3 may be made of a liquid-impermeable resin film such as cellophane. The cover film 3 in this embodiment is colorless and transparent over the entire surface thereof, but this is not a limitation to the present invention. The cover film 3 is generally identical in dimensions to the film backing 1. The cover film 3 is marked off into rectangular cover sections 3A each including the hollow space 1D in the film backing 1. The cover sections 3A may be defined by, for example, perforations 3B. The cover sections 3A are easily separable from each other. Some or all perforations 3B may be replaced with grooves of which depth is smaller than the thickness of the cover film 3.

The skin test device S2 is used as shown in FIGS. 8A-8C.

When the skin test device S2 is used, the adhesive layers 1F are brought into contact with the skin to stick the film backing 1 to the skin (FIG. 8A).

Then, samples are placed in the hollow spaces 1D. The samples 2 are placed in all hollow spaces 1D in this embodiment, but it is not necessary to supply all hollow spaces 1D with samples.

When the samples are placed in the hollow spaces 1D, the cover film 3 is put thereon to cover the exposed surface of the film backing 1. This prevents the samples from running out the hollow spaces 1D. (FIG. 8B). In order to facilitate this operation, an adhesive is previously applied to the surface of the cover film 3 to be brought into contact with the film backing 1. In this event, the hollow spaces 1D are received in the cover sections 3A of the cover film 3.

The samples are left to stand to contact the samples incorporated in the hydrogel with the skin.

After the lapse of a certain period of time, allergic reactions are developed which cause hives or blisters and which ensure identification of causative allergens for allergen samples 2 that are responsible for the reactions. Since the film backing 1 is made see-through, the change in skin condition can be visually observed throughout the test without removing the skin test device S2 staying on the skin.

When enough allergic reactions arc developed to ensure identification of causative allergens for allergen samples that are responsible for the reaction, the cover sections 3A associated with the hollow spaces 1D in which the allergen samples are placed are removed to remove the samples or apply a neutralizing agent (FIG. 8C).

Patch testing is continued for regions where allergic reactions are not fully developed.

As a modification of the skin test device S2, a skin test device without projected rim 1E or equivalent thereof would be contemplated. In such a case, an adhesive is spread over the entire surface of the flat surface of the film backing that is to be brought into contact with the skin.

Alternatively, the cover film 3 as shown in FIG. 8B may be provided beforehand. More specifically, the film backing 1 may be combined with the cover film 3 as a unit and different samples may be placed in the hollow spaces 1D.

It is needless to say that a protective release liner as described above may be applied to the skin test device S2.

What is claimed is:

1. A skin test device comprising:
   a film backing; and
   a sample that is placed on one surface of said film backing, the sample containing a suspected allergen, wherein
   said film backing is transparent of said film backing at least at the portion where said sample is placed, and
   said film backing is marked off into divisions, the divisions each having a different sample placed thereon, wherein
   the divisions of said film backing are easily separable from each other.

2. The skin test device as claimed in claim 1, wherein said film backing is marked off into a matrix of the divisions.

3. The skin test device as claimed in claim 1, wherein adjacent divisions are marked off by grooves that do not penetrate through said film backing.

4. The skin test device as claimed in claim 1, wherein adjacent divisions are marked off by perforations.

5. The skin test device as claimed in claim 1, wherein said film backing has a depression formed in one surface thereof and said sample is placed inside the depression.

6. A skin test device comprising:
   a film backing; and
   a sample that is placed on one surface of said film backing, the sample containing a suspected allergen, wherein
   said film backing is see-through from only one side to the other of said film backing at least at the portion where said sample is placed, and
   wherein said film backing is marked off into divisions, the divisions each having a different sample placed thereon, wherein
   the divisions of said film backing are easily separable from each other.

7. A skin test device comprising:
   a film backing; and
   an adhesive layer provided at a predetermined position on one surface of said film backing to secure said film backing to the skin of a subject, at least two hollow spaces being provided in said film backing at a predetermined position, a hollow space of the at least two hollow spaces having such a size that is required to place a sample containing suspected allergen on the skin while keeping said film backing affixed to the skin, wherein
   said film backing is see-through at least along the periphery of the hollow space, and
   a see-through cover film that is adapted to be placed over the other surface of said film backing so that the hollow space is covered with said cover film while said film backing is secured to the skin, said cover film being for preventing the sample placed on the skin from running out of the hollow space, wherein said film backing has at least two hollow spaces formed therein and said cover film extends over all hollow spaces, said cover film being marked off into two or more cover sections that correspond to the respective hollow spaces so that the cover sections are easily separable from each other.

8. The skin test device as claimed in claim 7, wherein a keeper is provided inside the hollow space to keep the sample.

9. The skin test device as claimed in claim 8, wherein the keeper is a transparent type keeper.

10. The skin test device as claimed in claim 7, wherein said cover film is configured so that said cover film covers the entire surface of said film backing and is integrally fixed to the surface of said film backing, the sample being placed on the portion of said cover film facing to the hollow space in said film backing.

11. The skin test device as claimed in claim 10, wherein said cover film being provided so that said cover film covers the at least two hollow spaces and being marked off into two or more cover sections that correspond to the respective hollow spaces, the cover sections being easily separable from each other so that the separated cover section can be removed from said film backing when necessary.

12. The skin test device as claimed in claim 7, wherein a projected rim is formed from other portion on one surface of said film backing along the open edge of the hollow spaces in one surface of said film backing, and said adhesive layer is provided on the end surface of the projected rim.

13. A skin test device comprising:
    a film backing;
    an adhesive layer provided at a predetermined position on one surface of said film backing to secure said film backing to the skin of a subject, at least two hollow spaces being provided in said film backing at a predetermined location, a hollow space of the at least two hollow spaces having such a size that is required to place a sample containing suspected allergen on the skin while keeping said film backing stay on the skin, wherein
    said film backing is see-through from only one side to the other at least along the periphery of the hollow space, a see-through cover film that is adapted to be placed over the other surface of said film backing so that the hollow space is covered with said cover film while said film backing is secured to the skin, said cover film being for preventing the sample placed on the skin from running out of the hollow space, wherein said film backing has at least two hollow spaces formed therein and said cover film extends over all hollow spaces, said cover film being marked off into two or more cover sections that correspond to the respective hollow spaces so that the cover sections are easily separable from each other.

14. A skin test device comprising:
    a film backing;
    an adhesive layer provided at a predetermined position on one surface of said film backing to secure said film backing to the skin of a subject; and
    at least one keeper region that is provided on one surface of said film backing, said keeper region being for keeping a sample that contains a suspected allergen, wherein
    said film backing is see-through from either side at least at the portion corresponding to said keeper region, and wherein said film backing is marked off into divisions, the divisions each having a different keeper, wherein
the divisions of said film backing are easily separable from each other.

15. The skin test device as claimed in claim 14, wherein said keeper region is a depression formed in one surface of said film backing.

16. The skin test device as claimed in claim 14, wherein said keeper region is keeper that is provided on one surface of said film backing to keep the sample.

17. The skin test device as claimed in claim 16, wherein said keeper is provided inside the depression.

18. A skin test device comprising:
a film backing;
an adhesive layer provided at a predetermined position on one surface of said film backing to secure said film backing to the skin of a subject; and
at least one keeper region provided on the surface of said film backing where said adhesive layer is provided, said keeper region being for keeping a sample that contains a suspected allergen, wherein
said film backing is see-through from only one side to the other at least at the portion corresponding to said keeper region, and
wherein said film backing is marked off into divisions, the divisions each having a different keeper, wherein
the divisions of said film backing are easily separable from each other.

19. The skin test device as claimed in claim 1, wherein said film backing is see-through over the entire surface thereof.

20. The skin test device as claimed in claim 1, wherein said film backing is made of silicone.

* * * * *